(12) United States Patent
Howland

(10) Patent No.: US 8,408,096 B2
(45) Date of Patent: Apr. 2, 2013

(54) SHAVING/CUTTING DEVICE WITH DIRECTLY DEPOSITED RAZOR STRUCTURES

(76) Inventor: Herbert A. Howland, Manomet, MA (US)

(*) Notice: Subject to any disclaimer, the term of this patent is extended or adjusted under 35 U.S.C. 154(b) by 819 days.

(21) Appl. No.: 11/786,422

(22) Filed: Apr. 10, 2007

(65) Prior Publication Data

US 2007/0234852 A1    Oct. 11, 2007

Related U.S. Application Data

(60) Provisional application No. 60/790,350, filed on Apr. 10, 2006.

(51) Int. Cl.
*B21K 11/00* (2006.01)

(52) U.S. Cl. ............... 76/104.1; 76/DIG. 6; 76/DIG. 8; 76/107.1

(58) Field of Classification Search ......... 30/50, 346.54; 76/104.1, 107.1, 112, DIG. 6, DIG. 8; 83/13
See application file for complete search history.

(56) References Cited

U.S. PATENT DOCUMENTS

| | | | | |
|---|---|---|---|---|
| 3,703,766 | A * | 11/1972 | Tibbals | 30/346.53 |
| 5,056,227 | A * | 10/1991 | Kramer | 30/346.54 |
| 5,317,938 | A * | 6/1994 | de Juan et al. | 76/104.1 |
| 5,750,956 | A * | 5/1998 | Barnes et al. | 219/121.71 |
| 5,842,387 | A * | 12/1998 | Marcus et al. | 76/104.1 |
| 5,940,975 | A * | 8/1999 | Decker et al. | 30/346.54 |
| 7,124,511 | B2 * | 10/2006 | Hamada et al. | 30/346.53 |
| 7,357,052 | B2 * | 4/2008 | Denne | 76/104.1 |

* cited by examiner

*Primary Examiner* — Omar Flores Sanchez
(74) *Attorney, Agent, or Firm* — Maxine L. Barasch; Keohane & D'Alessandro PLLC

(57) ABSTRACT

A shaving/cutting device with directly deposited (formed) razor structures without the use of intermediate adhesives. The device is in the form of a substantially flat substrate with miniature razors that have been directly deposited and formed onto the surface of the substrate. The substrate is of a rigid or flexible nature. The substrate is substantially thin and is therefore flexible and its shape is rectangular, circular or oval in nature. The razors are substantially deposited in plurality as an array formation onto the surface of the substrate. In most cases the razor array formation is in the form of parallel, curved and concentric nature. Flat mesa structures that are substantially the same height as the razor structures are incorporated in the razor array formations. The methods of manufacturing one or more directly deposited razor structures and mesa structures is disclosed.

6 Claims, 10 Drawing Sheets

SHAVING/CUTTING DEVICE WITH DIRECTLY DEPOSITED RAZOR STRUCTURES

CROSS-REFERENCES TO RELATED APPLICATIONS

I hereby claim prior filing related to the provisional patent filed Apr. 10, 2006 U.S.60/790,350.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

This invention relates to shaving devices and in particular a wet-shaving system that uses directly deposited razors instead of the traditional and individually fabricated blades that are usually assembled into a substantially complicated cartridge. A new and non-traditional method of manufacturing razor blades is used to form directly deposited razor structures.

BRIEF SUMMARY OF THE INVENTION

In one aspect, the device is as a hand held device used for wet-shaving facial and body hair in a unique and novel way. In this aspect the device is a thin, flat flexible substrate (pad) that has a unique array of durable yet flexible miniature sized razor blade structures on the surface. The razor structures are deposited (formed) directly onto the substrate surface using a novel manufacturing process. During the forming process the razor structure base adheres directly to the substrate surface without the use of intermediate adhesives. The resulting razor structures and substrate are very flexible and can conform to facial and body contours. Mesa structures within the razor array are also formed during the manufacturing process. These mesa structures act so as to help to prevent the razors from penetrating the skin. The razor and mesa structures are arranged in such a way that, when the device is used in a single or back and forth or circular shaving motion against the skin, it is an effective and intrinsically safe method of shaving facial and body hair. The razors are very small in size thereby the razors will abrade or cut the tips of the hair rather than initially cutting it directly at the surface of the skin. Continued motion of the device will cleanly cut the hair to the surface of the skin.

In an additional aspect the device can be held in the hand as a pad or can be affixed to a traditional shaving handle therefore, making it easy to integrate with the traditional shaving system.

In an additional aspect the trailing edge of the razor rows are designed to channel shaved material away.

In an additional aspect a small curved tubular chute is affixed to the trailing edge of the device, which will clear shaved material off the skin during the shaving stroke.

Related to the novel method of manufacturing is the aspect that the tooling used in this method can be easily modified to make different arrangements of the razor structures and arrays on the substrate. This allows the device to be easily modified to allow for a variety of shaving requirements, thereby modifications are made at lower cost than traditional tooling.

An additional embodiment is the aspect that the device has the above features but is instead used in an industrial application where the mechanical shaving/abrading and removal of materials that require a strong and durable razor material and the contouring effect is afforded by this device. Furthermore, the device is fabricated with materials that are application specific. Furthermore, a rigid substrate is used when flat (planar) shaving/abrading removal of material is required. Furthermore the device can be integrated into motorized disc or belt applications.

In another additional embodiment is the aspect that the device has the above features but is instead used in medical/surgical applications where the careful scraping or shaving or removal of skin tissue, bone, and bio-material is required. Furthermore, the device is fabricated using materials that are application specific.

In an additional embodiment is the aspect that the device is made using a novel manufacturing technique. This novel method is used to produce razor structures in very small scale including the nano-scale. Therefore, this device will be very likely to have many uses and benefits in the nano-technology industry.

The shaving/cutting device is manufactured in such a way that someone skilled in the art of nanomachining or nanofabrication techniques, micromachining, MEMS (micro electromechanical systems) and NEMS (nano electromechanical systems) techniques, thin-film deposition, and photochemical machining would be able to understand how to make this device.

BRIEF DESCRIPTION OF THE SEVERAL VIEWS OF THE DRAWING(S)

FIG. 1A: Front view of a rectangular substrate of the approximate dimensions 32 mmL×6.5 mmW×0.125 mm thick showing an array of curved razor and mesa structures.

FIG. 1B: is an angled aspect view of FIG. 1A.

FIG. 2A: Front view of a rectangular substrate of the approximate dimensions 32 mmL×10 mmW×0.125 mm thick showing opposite arrays of curved razor and mesa structures.

FIG. 2B: is an angled aspect view of FIG. 2A.

FIG. 3A: Front view of a circular substrate of the approximate dimensions 50 mm diameter×1.0 mm thick showing a quadrant of opposite arrays of curved razor and mesa structures.

FIG. 3B: is an angled aspect view of FIG. 3A.

FIG. 4: Depicts a cut-away of the rectangular view in FIG. 1B, a close up view of a razor structure and another angled view showing the addition of additional mesa in the lower right and left corners.

DETAILED DESCRIPTION OF THE INVENTION

Figure 1A:
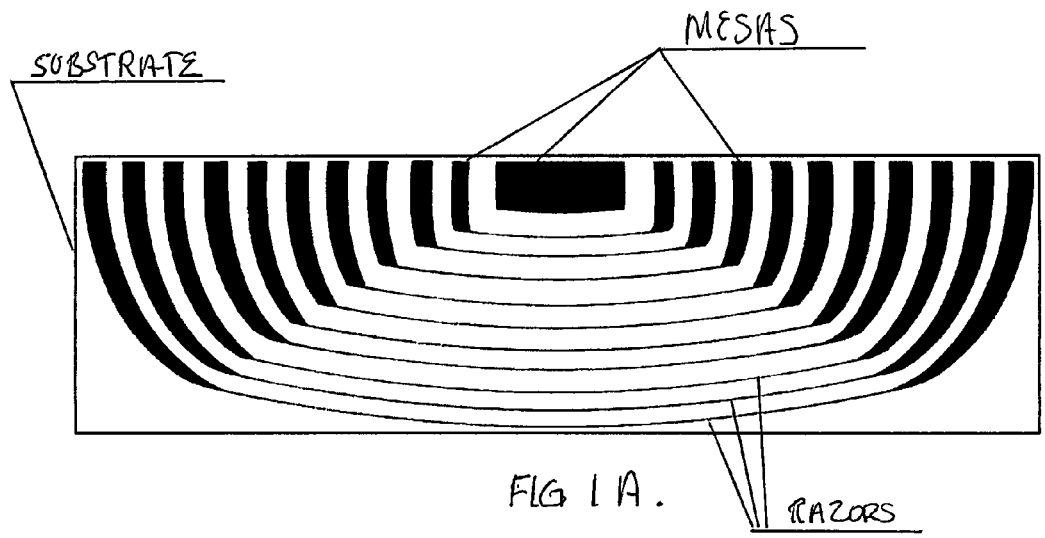
Figure 1B:
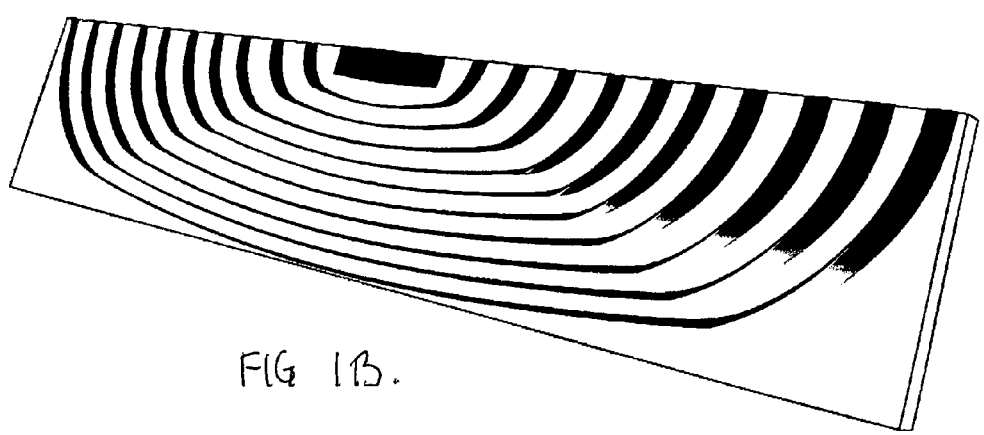
Figure 2A:
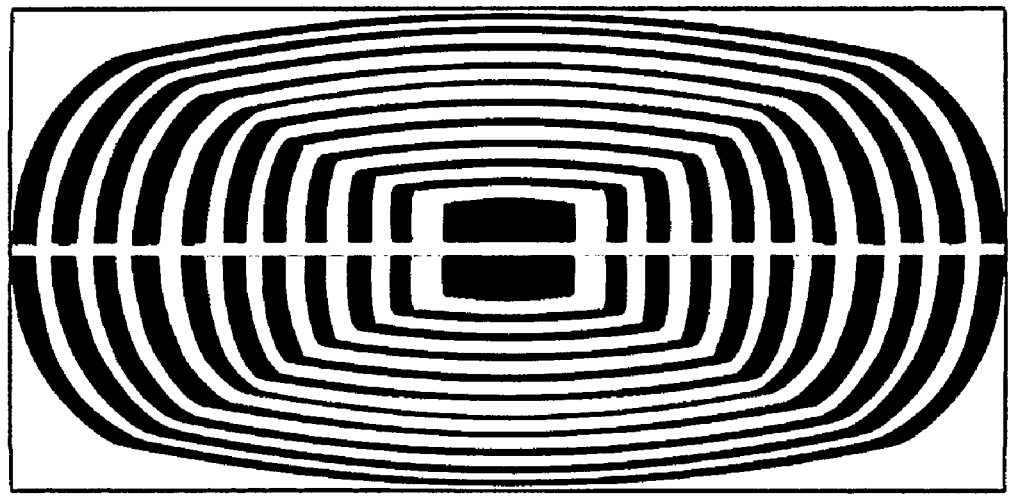
Figure 2B:
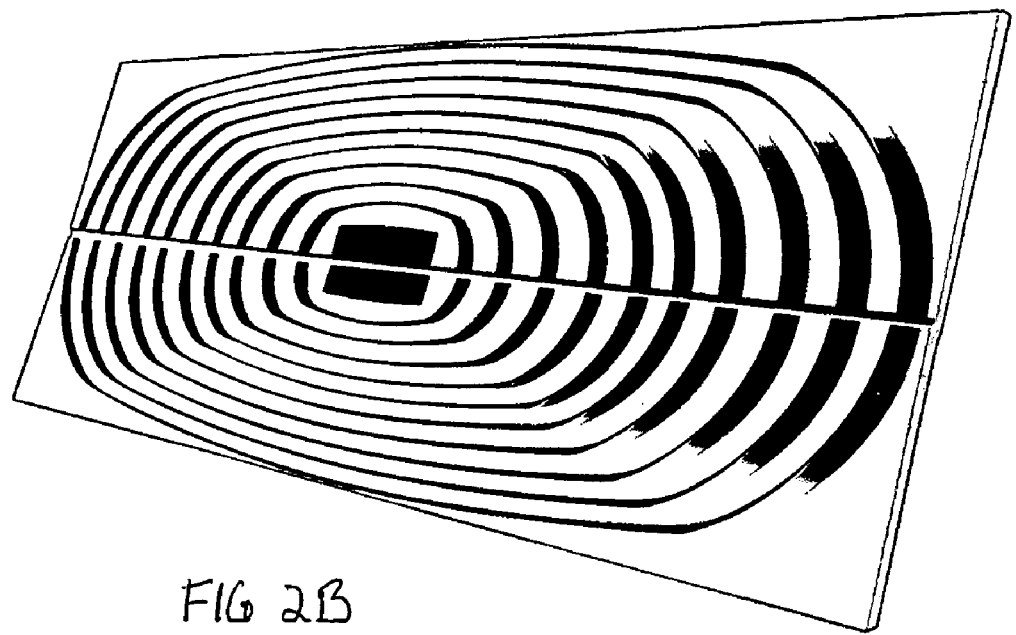
Figure 3A:
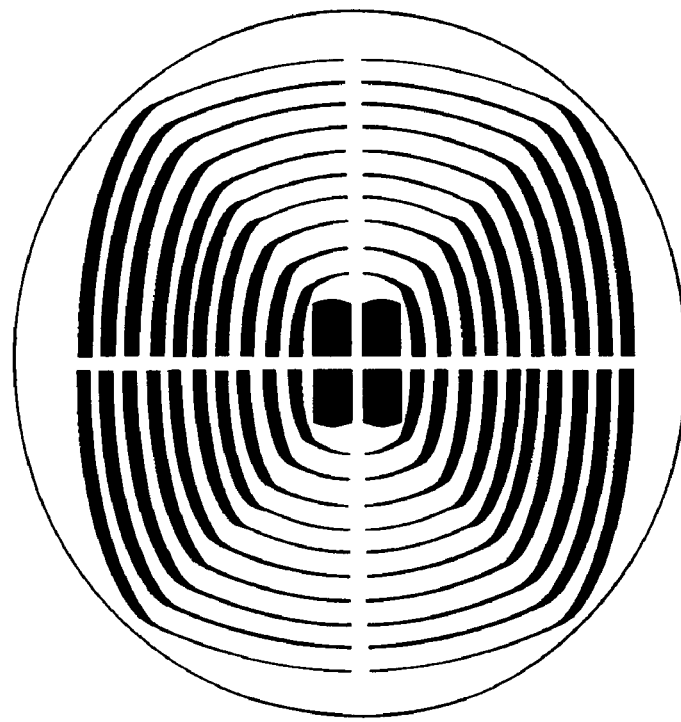
Figure 3B:
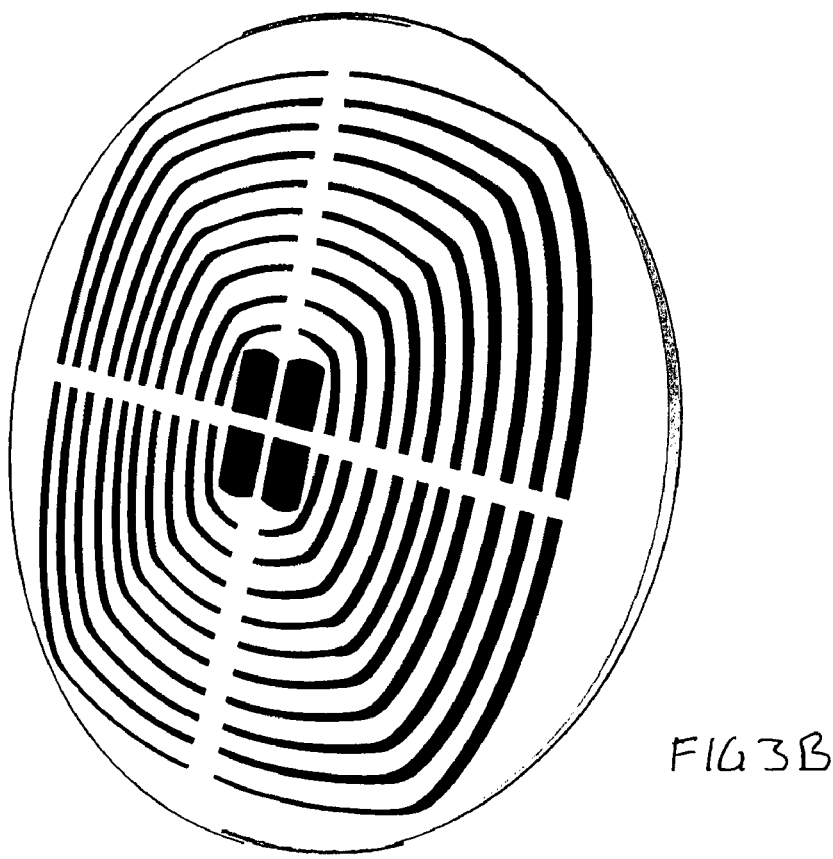
Figure 4:
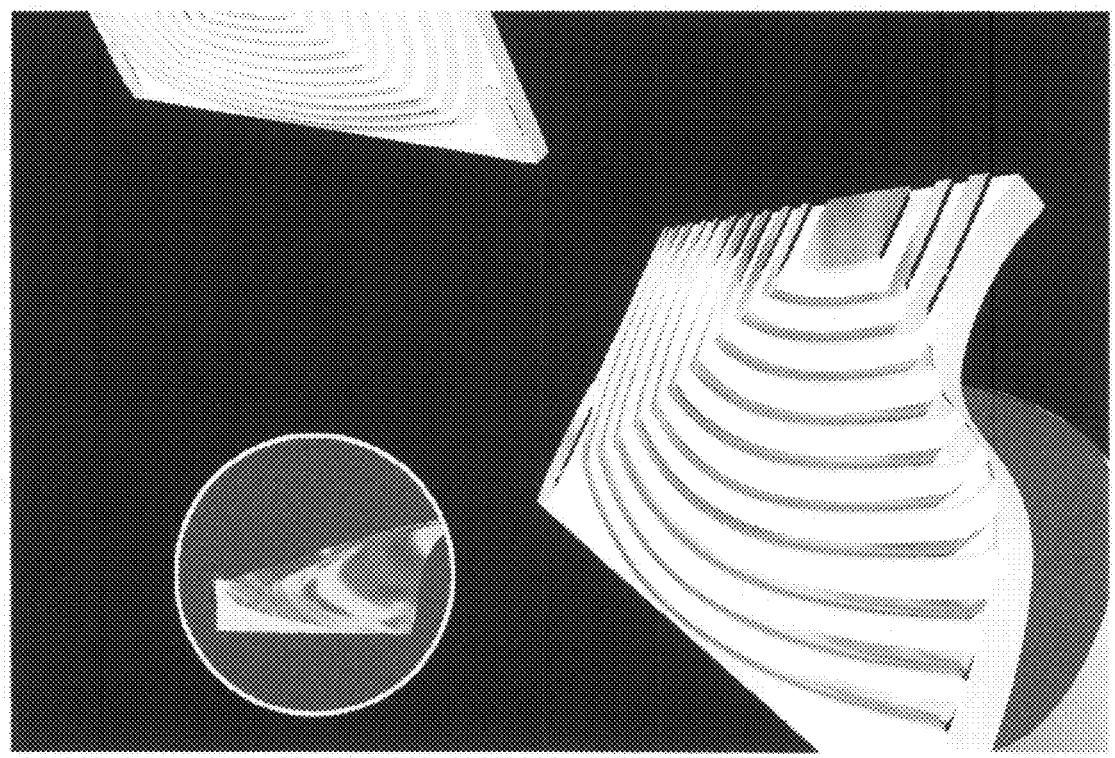
Figure 5:
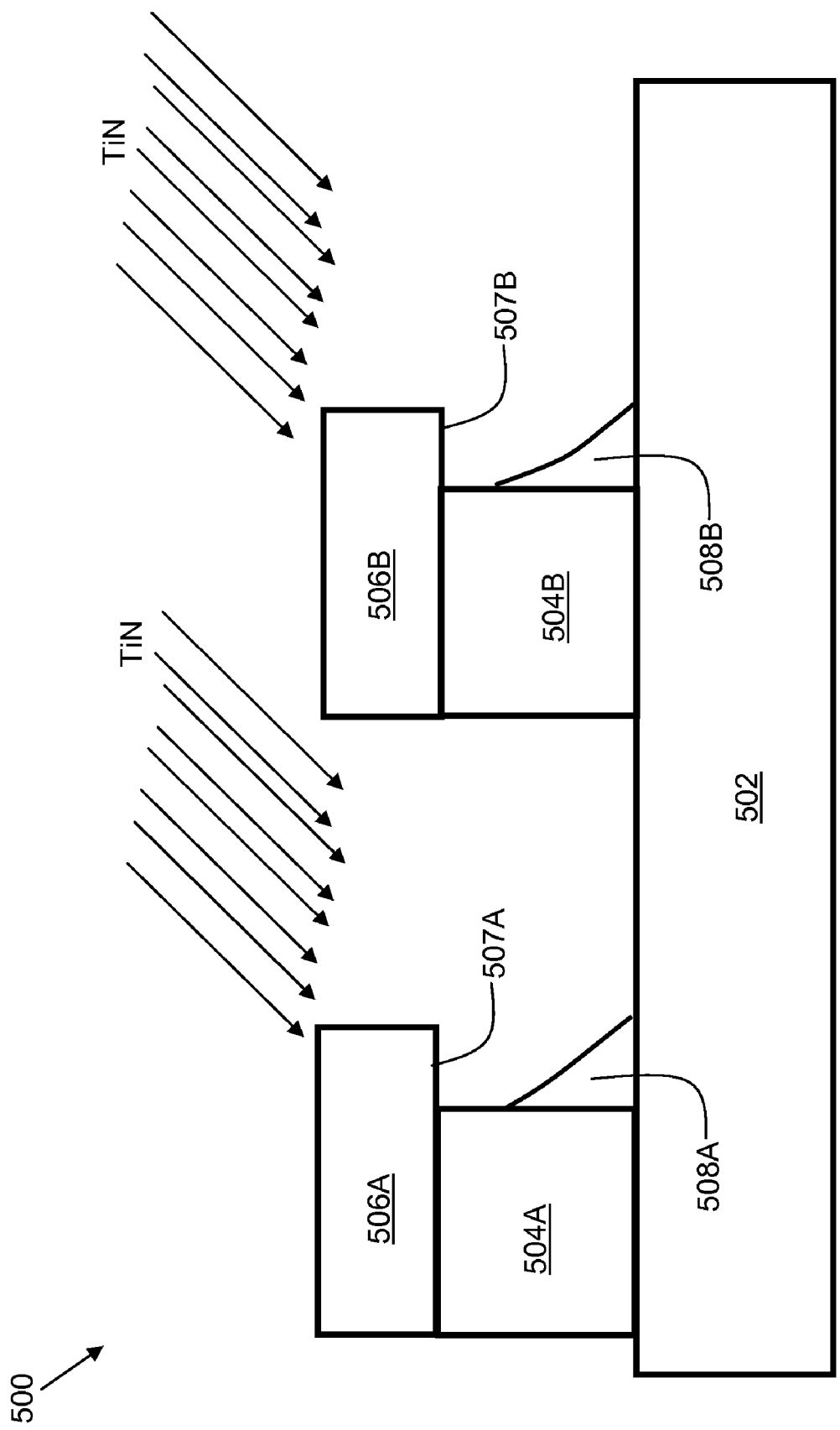
FIGS. 5-9 show various stages of the fabrication process.
Figure 6:
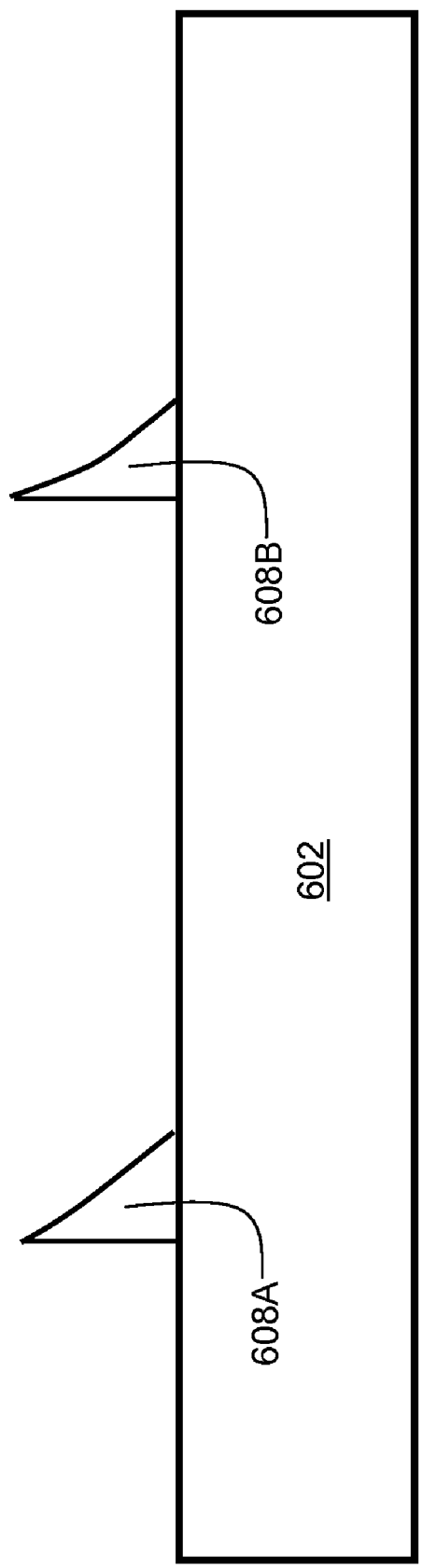

A shaving/cutting device with directly deposited (formed) razor structures without the use of intermediate adhesives. The device is in the form of a substantially flat substrate with miniature razors that have been directly deposited and formed onto the surface of the substrate. The substrate is of a rigid or flexible nature. The substrate is substantially thin and is therefore flexible and its shape is rectangular, circular or oval in nature.

The razors are substantially deposited in plurality as an array formation onto the surface of the substrate. In most cases the razor array formation is in the form of parallel, curved and concentric nature.

Flat mesa structures that are substantially the same height as the razor structures are incorporated in the razor array formations. The methods of manufacturing one or more directly deposited razor structures and mesa structures is disclosed below.

A method for manufacturing directly deposited razor structures onto to a flexible or rigid planar substrate which includes the steps:

1. Laminating or depositing the first photo-resist onto the surface of the substrate then imaging and developing said photo-resist to achieve suitable aspect ratios for razor structure formation.

Re-laminating with a second photo-resist over the first photo-resist and imaging in an off-set manner in relation to the top edge of the first photo-resist, thereby achieving an overhang of the second photo-resist over the top edge of the first photo-resist.

Whereby, the device has been processed to this point with multiple repeating devices on the substrate.

2. Whereby, the device is entered into a vacuum chamber for the purpose of depositing a monolithic layer of titanium nitride via sputtering.

Whereby the source angle of deposited material causes a buildup of razor material along one vertical face of the first photo-resist wall.

Whereby, the above mentioned overhang presents a shadowing effect to the deposited material during the deposition process, thereby effectively separating the formed razor structures from the monolithic layer of deposited material.

Whereby, the device is then removed from the vacuum chamber and processed with a wet-chemical photo-resist remover. The monolithic over-layer of deposited material is washed away along with both the first and second photo-resist and the razor structures are left free standing on the surface of the substrate.

Whereby the perimeter of each device is cut from the substrate for final use or subsequent assembly.

3. Whereby, in an alternate method, no second photo-resist is used and instead a thin but tough precision stencil mask that has been pre-patterned with a design which allows the same over-hang effect over the top edge of the first photo-resist as described above is used. This stencil mask is then placed in intimate contact with the top of the first patterned photo-resist. The mask and substrate are affixed together and processed as in part 2 above.

Whereby in step 2 the stencil is lifted away from the substrate carrying with it the monolithic over-layer of deposited material. Whereby the subsequent step in part 2 is to wet-chemical wash away only the first photo-resist.

Method 1.

A substrate is coated with a thin photo-sensitive coating that is slightly thicker than the final height of the nano/micro razors. The coating is patterned by photo-lithographic means to define the nano/micro shaving razor rows. The coating is developed which leaves a 3-dimensional pattern of rows on the substrate surface. The vertical edge of these rows provide a physical foundation on which to form the leading edge of nano/micro razors.

The preferred razor material is TiN (titanium nitride) because of its exceptional durability, corrosion resistance and pleasing gold color. Furthermore, nitride, carbide, DLC (diamond-like carbon), and stainless steel materials are used as substitutes for TiN.

The nano/micro razors are deposited directly onto the substrate surface by the preferred means of reactively sputtering TiN (titanium nitride). Methods using high vacuum and ultra-high vacuum deposition techniques such as non-reactive sputtering, e-beam evaporation, resistive heat evaporation, plasma assisted metal ion deposition and laser ablation are used as a substitution for reactive sputtering.

Furthermore, one or a combination of the other materials described above are deposited first and TiN is used as an over coat modify the hardness of the nano/micro shaving razors so as to suit different shaving requirements.

A thin precision stencil mask with a similar pattern is then placed in intimate contact with the top of the patterned substrate. The mask aids in defining the razor structures when they are formed. The mask and substrate are fixtured together and placed into a high vacuum chamber.

TiN is reactively sputter deposited at an angle of approximately 45 degrees from the plane of the substrate surface and which is perpendicular to the patterned razor rows. The deposited TiN fills in the spaces between the patterned rows and builds up in such a way as to form a razor shape. After the TiN is deposited, the mask and substrate are removed from the vacuum chamber. The mask is lifted away from the substrate. The excess deposited TiN is lifted away with the mask. The original photo-sensitive coating pattern on the substrate is then wet chemically washed away. The TiN deposited razor and mesa structures are then left free standing on the surface of the substrate.

Method 2.

The steps for an alternative method of manufacturing the razor structures without the support of photoresist are described in Part M2.

Part M1. Steps for Manufacturing the Device Using Method 1.

Referring to FIGS. 5-9 which show various steps in the fabrication process, the following steps are performed:

1. A flat substrate sheet 502 (FIG. 5) of the preferred dimensions 8.0"×10.0"×0.125 mm thick is cleaned using standard precision-cleaning techniques.

2. The substrate sheet 502 is then coated one side with a heat laminated photoresist. The preferred thickness of the photoresist is 0.005". Note: The thickness of the photoresist determines the maximum height of the razor and mesa structures therefore, thicker photoresist will allow more TiN to be deposited and the razor and mesa structures will be higher. Vice versa is true. Using nanolithographic techniques the razor structures can be formed in the nano scale range.

3. The coated substrate sheet has the razor array pattern (straight, spiral or otherwise) imaged multiple times onto the substrate photoresist coating using standard photolithography techniques. Multiple images allow more devices to be manufactured at the same time.

4. The patterned image on the photoresist coating is wet chemically developed. This leaves an array of rectangular (three dimensional) shaped photoresist rows on the surface of the substrate (504A, 504B). Note: It is preferable to slightly overdevelop the photoresist coating. This has the effect of making the vertical sidewall of the photoresist slightly convex (see regions 804A and 804B of FIG. 8). This facing (slightly convex) vertical side-wall of the rectangular photoresist rows, with respect to the direction of TiN deposition, provide the foundation to form the leading edge of the TiN nano-micro razors.

5. A precision stencil mask (506A and 506B of FIG. 5) of thin, but taught, stainless steel is fabricated with standard photo-chemical machining or laser cutting techniques. The preferred thickness of this stencil is 0.003". The stencil is the same 8"×10" dimensions and has the same multiple patterns of razor structures as the substrate. However the images are slightly modified (as outlined in step 6.). Alternatively, instead of using a stencil mask, regions 506A and 506B of FIG. 5 may comprise a second photoresist region.

6. The stencil mask is aligned (registered) on the top of the patterned substrate and is mechanically fixtured to the substrate as an assembly. The mask is in intimate contact with the top surface of the photoresist areas. The mask has open and land areas with the same corresponding features as the patterned substrate. However, the corresponding land areas of the mask, with respect to the top surface of the photoresist rows on the substrate, are slightly wider on one edge. This creates a slight overhang (507A, 507B of FIG. 5) of the mask at the intersection of the top surface edge of each photoresist row and its vertical side-wall with respect to the direction of the TiN deposition. This overhang acts as a partial shadowing effect to the deposited TiN. This overhang therefore, acts to define the top sharp edge of the formed razor structure by preventing the build up excess of deposited TiN at this intersection. The adjacent edge of the stencil, with respect to the TiN deposition, also provides a partial shadowing effect to the deposited TiN. This partial shadowing effect, therefore, acts to define the trailing (base) edge of the razor structure on the surface of the substrate.

7. The mask and substrate assembly are put into a high vacuum chamber to have TiN reactively sputter deposited at an angle of approximately 45 degrees from the plane of the substrate surface and perpendicular to the patterned rows. The deposited TiN fills in the spaces between the rows in such a way as to collect on the slightly convex photoresist side-walls and to form a base on the substrate (see 808A and 808B of FIG. 8). The mesa areas of the pattern (see 1020, the mesa of FIG. 10 and FIGS. 1A and 1B, 1018 is a sharp razor edge) are considered to be parallel with respect to the TiN deposition. Therefore the TiN collects in this area in such a way as to form a flat mesa surface. The TiN deposition is pre-determined and is stopped when a complete razor structure is formed.

8. After the TiN is deposited the stencil mask and substrate are removed from the vacuum chamber. The stencil mask is carefully lifted away from the substrate. The excess deposited TiN is lifted away with the mask. The original photoresist coating pattern on the substrate is then wet chemically washed away. The TiN deposited razor and mesa structures are then left free-standing on the surface of the substrate (see FIGS. 6 and 9).

9. The individual NANO SHAVING/CUTTING DEVICE arrays are cut from the substrate for use.

Part M2: STEPS FOR ALTERNATIVE METHOD OF MANUFACTURING USING METHOD 2.

Razors are formed on the substrate without the support of photoresist.

1. A thin precision stainless steel stencil mask, with the preferred dimensions of 8"×10'×0.006" thick is coated with photoresist on both sides. One side of the stencil is imaged with multiple nano/micro razor array patterns using photolithography techniques. Then the photoresist image is wet chemically developed.

3. The precision pattern on the stencil mask is then chemically milled in such a way as to create a tapered cavity (on one side only), around the open patterned areas of the stencil. Then the photoresist is wet chemically stripped away.

4. The stencil is then placed in direct intimate contact with the surface of a flat clean substrate sheet of the preferred dimensions 8.0"×10.0"×0.125 mm. The cavity side of the stencil faces the substrate.

Figure 7:
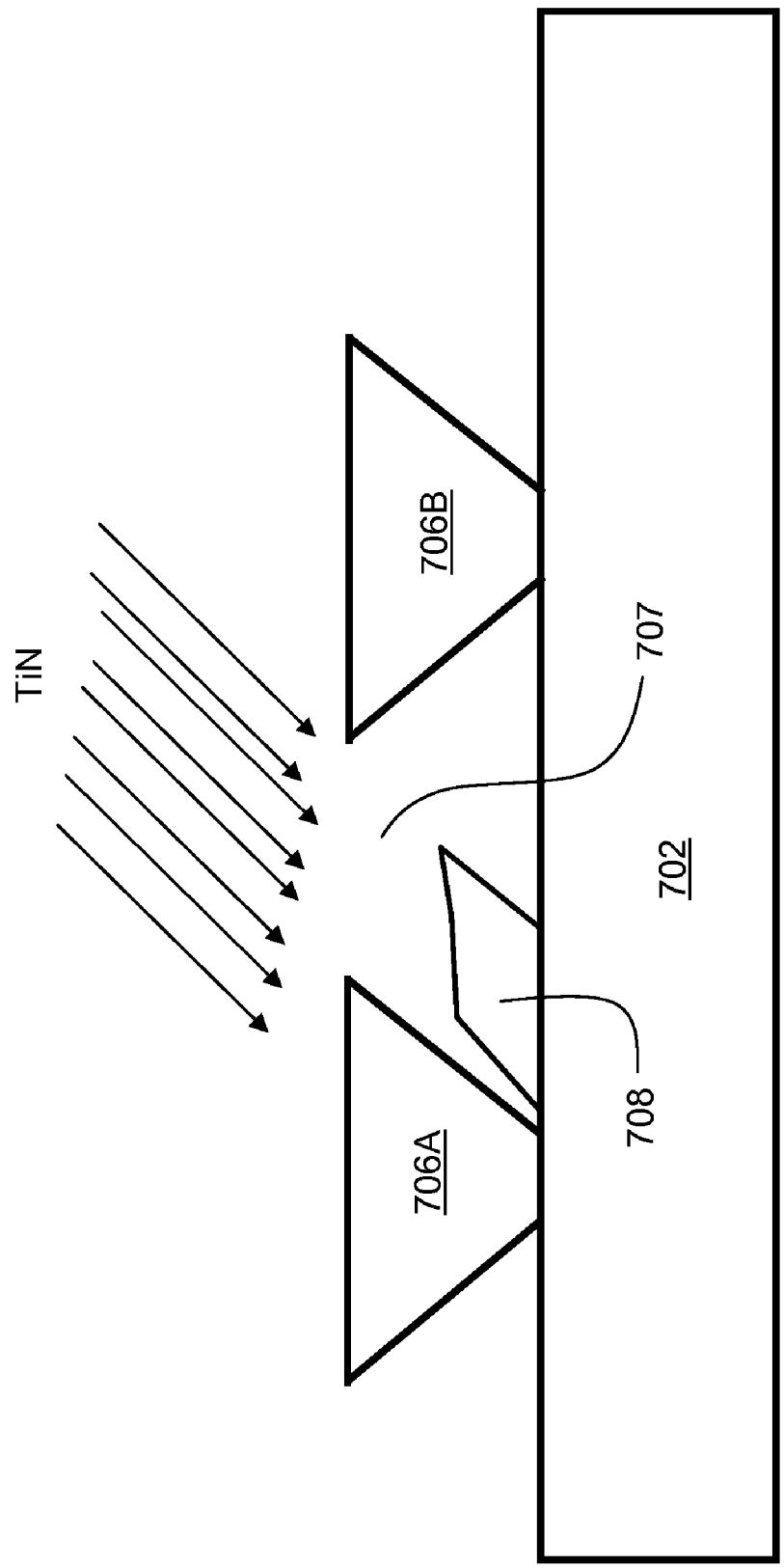
Figure 8:
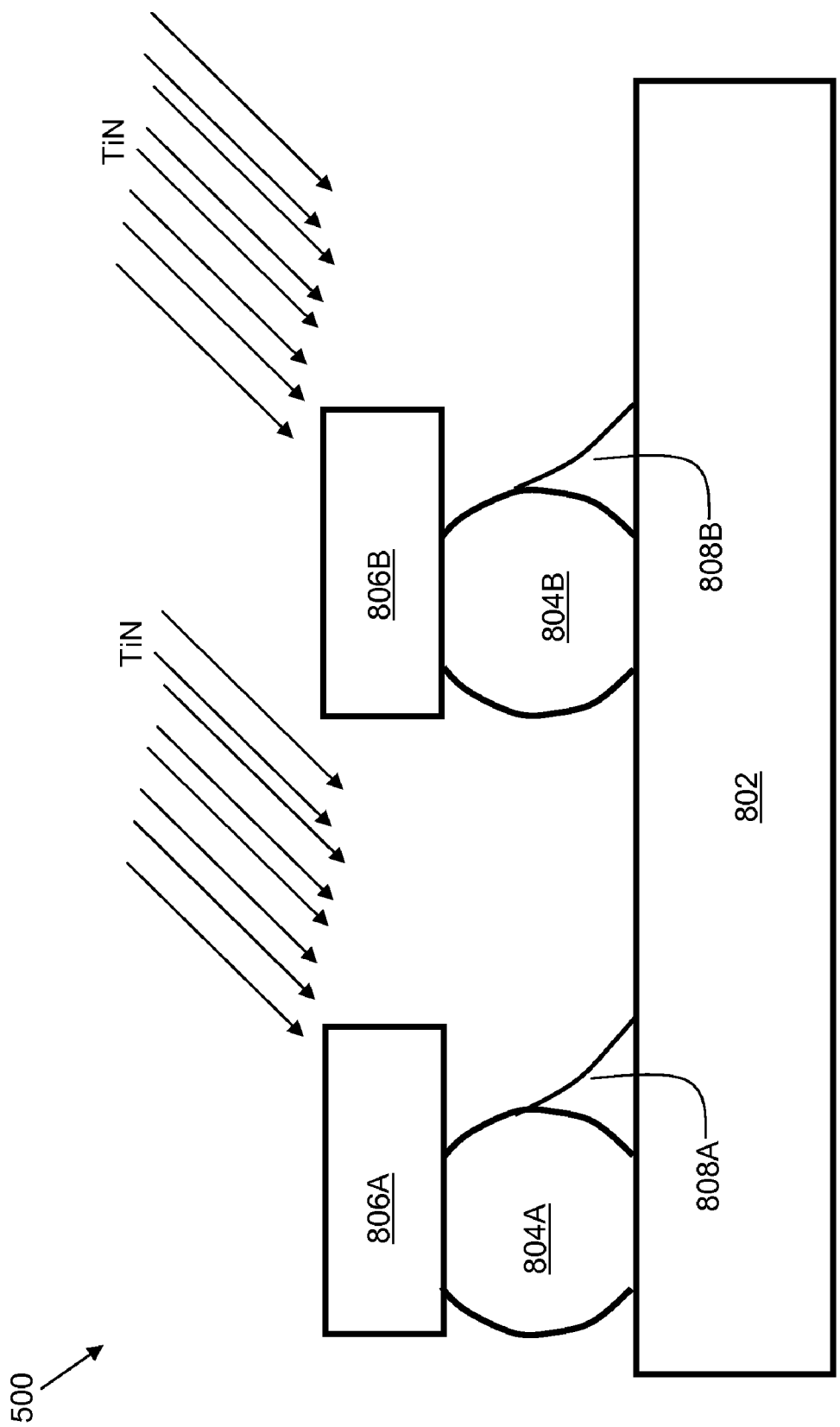
Figure 9:
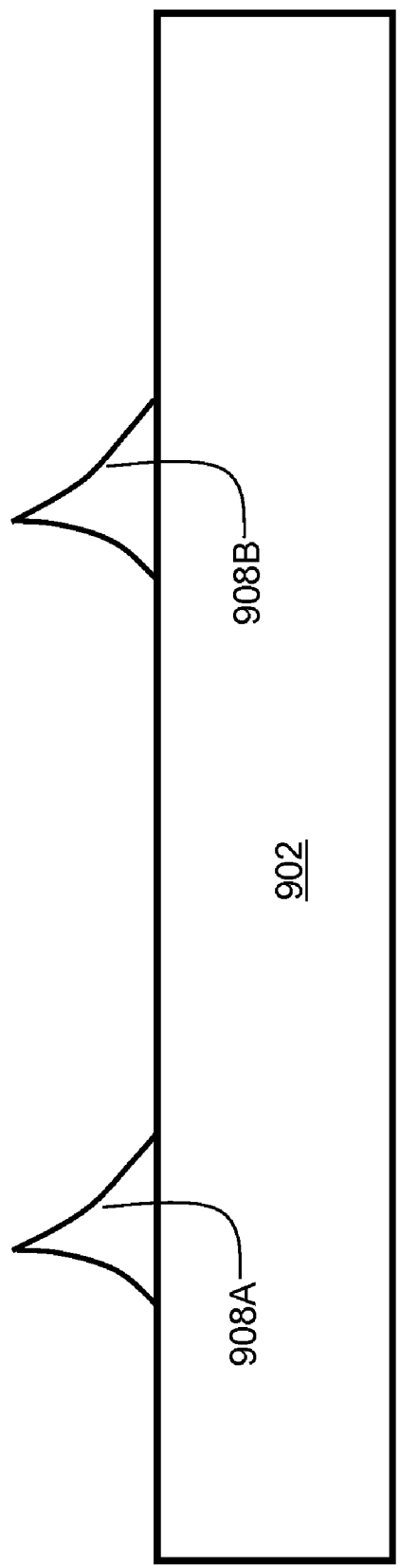
Figure 10:
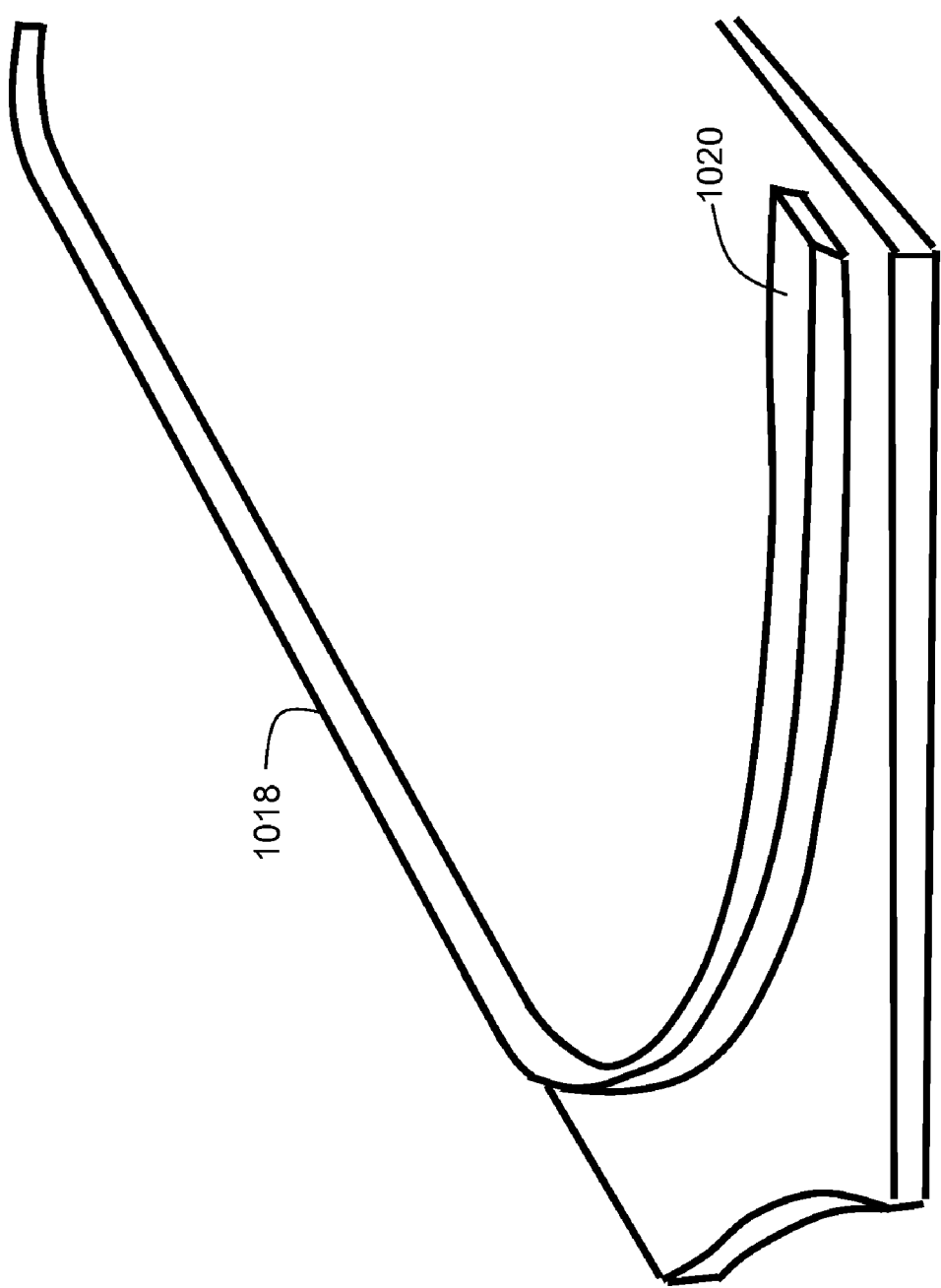
FIG. 10 shows a perspective view of a mesa.

5. As shown in FIG. 7, the mask (706A, 706B) and substrate (702) are fixtured together and are placed into a high vacuum chamber. TiN is reactively sputter deposited at an angle of approximately 45 degrees from the plane of the substrate surface and which is perpendicular to the leading edge of the patterned nano/micro razor rows. TiN passes through the narrow patterned open areas (707) of the stencil mask and onto the surface of the substrate. Locally, the cavity on the underside of the stencil allows the TiN to deposit through the open areas in such a way as to prevent the TiN from adhering to the stencil walls. The TiN then deposits in such a way as to form free-standing razor and mesa structures (708).

6. After the TiN is deposited the stencil mask and substrate are removed from the vacuum chamber. The stencil mask and substrate are unfixtured. The stencil mask is lifted away from the substrate.

7. The TiN deposited razor and mesa structures are then left free-standing on the surface of the substrate. The individual nano/micro razor arrays are then cut from the substrate.

What is claimed is:

1. A method for directly depositing razor structures on a substrate surface comprising the steps of:
   a. depositing a first photo-resist layer on said substrate surface;
   b. exposing and developing said first photo-resist layer to form a first photo-resist region generally perpendicular to said substrate surface;
   c. providing a mask disposed on the first photo-resist region;
   d. positioning said mask such that said mask is generally parallel to and spaced from said first photo-resist region wherein said mask forms an overhang over said first photo-resist region;
   e. depositing a razor material directly onto the substrate surface at an angle to said substrate surface, said angle being such that said overhang provides blocking for said razor material from an upper portion of said first photo-resist region, whereby said razor material is deposited against said first photo-resist region and disposed directly on the substrate surface; and
   f. removing said mask and said first photo-resist region, thereby leaving said razor material that was deposited against said first photo-resist region in step e, disposed directly on the substrate surface.

2. The method of claim 1 wherein said mask is formed by (1) depositing a second photo-resist layer on said first photo-resist layer, and (2) exposing and developing said second photo-resist layer to form a second photo-resist region.

3. The method of claim 1 wherein said mask is a pre-patterned stainless steel stencil.

4. The method of claim 1 wherein said razor material is titanium nitride.

5. The method of claim 1, further comprising overdeveloping the first photo-resist layer, thereby forming convex vertical sidewalls on the first photo-resist layer.

6. The method of claim 1, wherein the step of depositing a razor material is performed by e-beam evaporation.

* * * * *